(12) United States Patent
Jost et al.

(10) Patent No.: US 11,447,387 B2
(45) Date of Patent: Sep. 20, 2022

(54) DISPENSING DEVICE FOR PREVENTING MIXING OF LIQUIDS, SUPPLY SYSTEM, STORAGE SYSTEM AND SUPPLY METHOD IMPLEMENTING SUCH A DISPENSING DEVICE

(71) Applicant: ARYBALLE, Grenoble (FR)

(72) Inventors: Didier Jost, Narbonne (FR); Alan Jost, Varces Allieres et Risset (FR); Frederic Rustanys, Narbonne (FR)

(73) Assignee: ARYBALLE, Grenoble (FR)

( * ) Notice: Subject to any disclaimer, the term of this patent is extended or adjusted under 35 U.S.C. 154(b) by 0 days.

(21) Appl. No.: 17/296,715

(22) PCT Filed: Nov. 29, 2018

(86) PCT No.: PCT/FR2018/053055
§ 371 (c)(1),
(2) Date: May 25, 2021

(87) PCT Pub. No.: WO2020/109673
PCT Pub. Date: Jun. 4, 2020

(65) Prior Publication Data
US 2022/0033245 A1 Feb. 3, 2022

(51) Int. Cl.
*B67D 7/34* (2010.01)
*G01N 33/00* (2006.01)

(52) U.S. Cl.
CPC ......... *B67D 7/342* (2013.01); *G01N 33/0073* (2013.01)

(58) Field of Classification Search
CPC ........................ B67D 7/342; G01N 33/0073
See application file for complete search history.

(56) References Cited

U.S. PATENT DOCUMENTS 6,341,629 B1 * 1/2002 Clark ................. G01N 33/2829
141/59

FOREIGN PATENT DOCUMENTS

| EP | 2474500 A1 | 7/2012 |
| FR | 3052764 A1 | 12/2017 |
| GB | 2206561 A | 1/1989 |
| WO | 2015/194795 A1 | 12/2015 |

OTHER PUBLICATIONS

International Search Report dated Sep. 4, 2019 in corresponding application No. PCT/FR2018/053055; 5 pgs.

* cited by examiner

*Primary Examiner* — Jason K Niesz
(74) *Attorney, Agent, or Firm* — Maier & Maier, PLLC

(57) ABSTRACT

Dispensing device including a dispensing conduit configured to convey a liquid between a supply source and a tank, the dispensing conduit including a closure system having an open state and a closed state, an analysis system including an analysis chamber and an odor sensor, a central electronic system capable of placing the closure system in the open state if an odor signal delivered by the odor sensor matches the odor of the liquid intended to fill the tank, and placing the closure system in the closed state if an odor signal delivered by the odor sensor does not match the odor of the liquid intended to fill the tank.

21 Claims, 4 Drawing Sheets

DISPENSING DEVICE FOR PREVENTING MIXING OF LIQUIDS, SUPPLY SYSTEM, STORAGE SYSTEM AND SUPPLY METHOD IMPLEMENTING SUCH A DISPENSING DEVICE

FIELD

The invention relates to a device for preventing the mixing of liquids, with an electronic nose.

It concerns the field of dispensing liquid products, including petrochemical products, and is particularly suitable for deliveries of products such as fuels in service stations. The invention is intended to prevent possible mixing when delivering multiple products, collected from multiple containers, to their respective containers at the place of delivery.

BACKGROUND

Currently, there is no foolproof system on the market that is capable of preventing delivery errors due to the human factor, in a simple and transparent manner and requiring minimal maintenance. Mixtures resulting from human error entail significant costs for the companies providing transport, as well as damage to the image of the companies producing the delivered products and therefore a risk of operating losses.

For example, in the field of fuel delivery from the distributor to service stations, mixtures resulting from human error are still frequent despite systems already in place such as fool proofing or electronic systems.

A system already exists that uses an odor sensor for Volatile Organic Compounds (VOCs). Patent: WO 2015/194795. In this patent, the odor sensor is placed on the nozzle used to make the delivery and this sensor is inserted directly into the car's tank to perform the analysis. This device is intended for individuals or pump attendants and requires handling the nozzle with special care to avoid knocking or damaging the nose. This device is not really compatible with industrial and business use where manipulations are rougher, particularly during service station deliveries, where the fuel delivery hoses connecting the fuel bladders of the trucks to the tanks of the stations (which can also be called the delivery channel) are manipulated with a heavy hand.

SUMMARY

The present invention aims to overcome these problems.

To this end, according to a first aspect, the invention provides a dispensing device for preventing a mixing of liquids, each liquid being characterized by an odor, the dispensing device comprising:
- a dispensing conduit configured to convey a liquid between a supply source and a tank, the dispensing conduit comprising a passage for the liquid and a closure system having a passing state in which said closure system allows the flow of liquid in the passage of the dispensing conduit, and a blocking state in which said closure system prevents the flow of liquid in the passage of the dispensing conduit,
- an analysis system comprising an analysis chamber configured to collect a sample of liquid present in the dispensing conduit, and an odor sensor capable of delivering an odor signal representative of the odor of the liquid sample,
- a central electronic system connected to the closure system of the dispensing conduit and to the odor sensor of the analysis system, wherein the central electronic system is capable of:
- placing the closure system in the passing state if the odor signal delivered by the odor sensor matches the odor of the liquid intended to fill the tank,
- placing the closure system in the blocking state if the odor signal delivered by the odor sensor does not match the odor of the liquid intended to fill the tank.

The dispensing device can thus be controlled completely autonomously by the central electronic system, leaving no room for human error.

The dispensing conduit can extend between two opposite ends, the ends comprising attachment members configured to engage with respective complementary attachment members of the supply source and of the tank, at least the attachment member intended to engage with the complementary attachment member of the supply source being configured to establish a removable attachment.

The central electronic system may have an active state in which said central electronic system processes the odor signal delivered by the odor sensor, and a standby state, the dispensing device further comprising a detection system capable of detecting a situation of supplying liquid, the central electronic system being capable of entering the active state when a supplying situation is detected.

The detection system may comprise a presence sensor connected to the central electronic system and capable of delivering a connection signal representative of a connection of the supply source to the dispensing device, the central electronic system being capable of entering the active state when the presence sensor delivers the connection signal.

The detection system may comprise a motion detector arranged in the analysis chamber and connected to the central electronic system, the motion detector being capable of delivering a sampling signal representative of a sampling of liquid in the analysis chamber, the central electronic system being capable of entering the active state when the motion detector delivers the sampling signal.

The central electronic system in the active state may process the odor signal delivered by the odor sensor after a delay has elapsed.

The analysis chamber may comprise an inlet hole through which the liquid collected from the dispensing conduit enters the analysis chamber, and the motion detector may comprise a tab located at the inlet hole and mounted on an axis of rotation located above the inlet hole such that a rotation of the axis of rotation resulting from displacement of the tab under the effect of the liquid entering through the inlet hole causes delivery of the sampling signal.

The dispensing conduit may comprise a side wall around a central axis, defining the passage for the liquid, and a drainage system having an open state in which said drainage system allows the flow of liquid through a drainage port comprising a drainage port provided in the side wall of the dispensing conduit, and a closed state in which said drainage system prevents the flow of liquid through the drainage port, the drainage system being connected to the central electronic system, the central electronic system being capable of placing the drainage system in the open state if the odor signal delivered by the odor sensor does not match the odor of the liquid intended to fill the tank.

The analysis chamber may have a bottom and a side wall extending from the bottom to an upper opening to which the odor sensor is connected; the analysis system may comprise:

an inlet pipe extending between the dispensing conduit and the analysis chamber and open to the side wall of the analysis chamber near the bottom, an outlet pipe open to the side wall of the analysis chamber above the inlet pipe and defining a level for the liquid sample, a purge pipe open to the bottom of the analysis chamber, a first closure member having a passing state in which said first closure member allows the flow of liquid into the analysis chamber from the inlet pipe, and a blocking state in which said first closure member prevents the flow of liquid into the analysis chamber from the inlet pipe, a second closure member having a passing state in which said second closure member allows the flow of fluid between the upper opening and the odor sensor, and a blocking state in which said first closure member prevents the flow of fluid between the upper opening and the odor sensor.

The inlet pipe may have a cross-sectional area that is smaller than the cross-sectional area of the outlet pipe, and the purge pipe has a cross-sectional area that is smaller than the cross-sectional areas of the inlet and outlet pipes.

The analysis system may comprise a device for purging the analysis chamber connected to the outlet and purge pipes and open to the dispensing conduit.

The device for purging may comprise a vessel connected to the outlet and purge pipes and to a discharge pipe open to the dispensing conduit, the vessel having an air exhaust hole.

The device for purging may be open to the dispensing conduit via a floating ball check valve presenting a passing direction when the pressure in the device for purging is greater than the pressure in the dispensing conduit, and blocking direction when the pressure in the dispensing conduit is greater than the pressure in the device for purging.

The analysis chamber may comprise a protective plate perforated with multiple holes, located above the outlet pipe.

The analysis system may comprise an orientation system on which the analysis chamber is mounted so as to orient the analysis chamber in a vertical direction, the inlet, outlet, and purge pipes being flexible.

The dispensing device may further comprise a control unit which makes it possible to act on the autonomous electronic system in order to unlock the device and reset the system in the event of an error of liquid, in particular by the use of a key or a code.

According to a second aspect, the invention proposes a supply system comprising a dispensing device as defined above and a supply source, wherein the dispensing device is installed downstream of the supply source placed at a high point upstream so as to use gravitational force and obtain a naturally-induced pressure in order to supply the analysis chamber with liquid.

According to a third aspect, the invention provides a storage system comprising a dispensing device as defined above and a storage tank, the storage tank having a feed opening on which the dispensing device is mounted.

According to a fourth aspect, the invention proposes a supply method making use of a dispensing device as defined above, the dispensing device being interposed between a supply source and a tank, the method providing for:

placing the closure system in the passing state if the odor signal delivered by the odor sensor matches the odor of the liquid intended to fill the tank, placing the closure system in the blocking state if the odor signal delivered by the odor sensor does not match the odor of the liquid intended to fill the tank.

The supply method may provide for placing the active electronic system in an active state when a supplying situation is detected.

The supply method may provide for placing the first closure member in the blocking state as soon as the odor sensor has completed its analysis.

BRIEF DESCRIPTION OF THE DRAWINGS

Other objects and advantages of the invention will become apparent from reading the following description of particular embodiments of the invention, given as non-limiting examples, the description being made with reference to the accompanying drawings in which.

DETAILED DESCRIPTION

Figure 1:
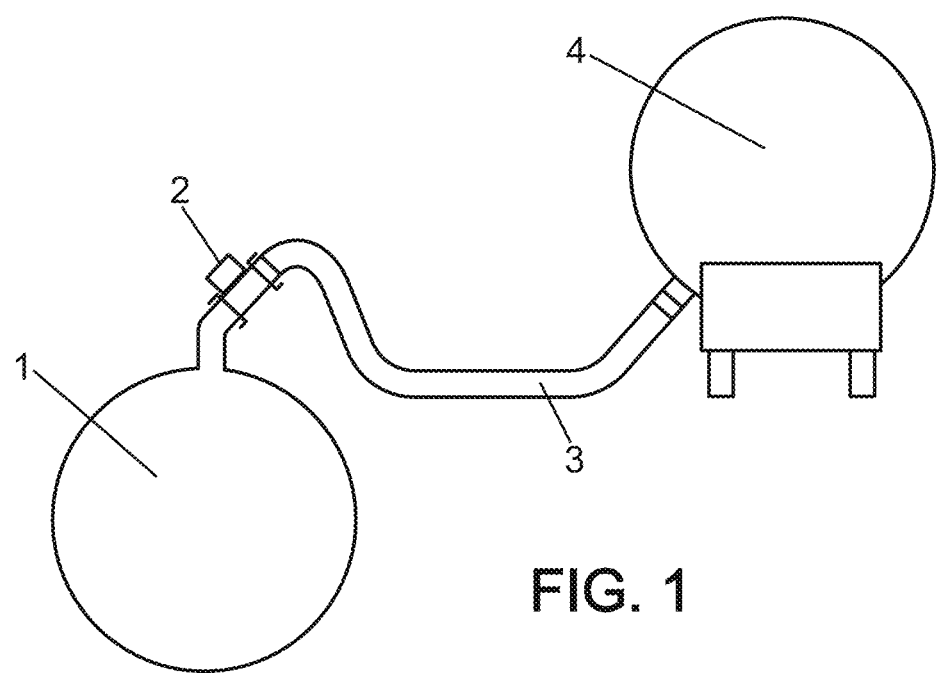
FIG. 1 is a representation of a system comprising a storage tank fed from a supply source supplying via a dispensing device according to one embodiment of the invention.

FIG. 1 shows a storage tank 1 to which liquid is to be delivered and which is equipped with the dispensing device 2, which in turn is connected to a supply source in the form of a delivery hose 3 which connects the storage tank to a tank or bladders of a vehicle 4 responsible for making deliveries.

Figure 2:
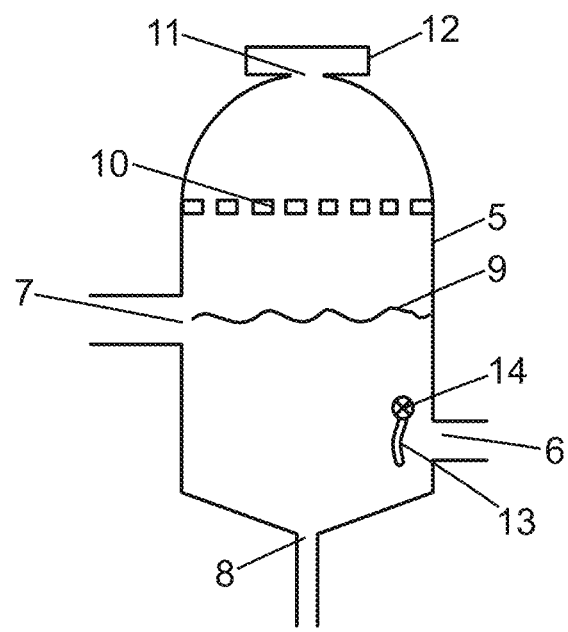
FIG. 2 is a cross-sectional representation of an analysis chamber of the dispensing device of FIG. 1.

FIG. 2 shows an analysis chamber 5 of the dispensing device. The analysis chamber has a bottom and a side wall extending from the bottom to an upper opening. The chamber comprises, with an inlet hole 6 for liquid in the side wall of the analysis chamber near the bottom, an outlet hole 7 in the side wall of the analysis chamber above the level of the inlet hole in order to define a maximum level of liquid in the analysis chamber, and a discharge hole 8 in the bottom of the analysis chamber for purging the analysis chamber. The analysis chamber has an upper opening 11 opposite the bottom and to which is connected an odor sensor 24 capable of delivering an odor signal representative of the odor of the liquid sample. The upper opening is provided with a solenoid valve 12 forming a second closure member as will be apparent in the remainder of the description, to protect the odor sensor.

The analysis chamber has a protective plate 10 perforated with multiple holes, located above the outlet pipe.

A motion detector is arranged in the analysis chamber 5. The motion detector is capable of delivering a sampling signal representative of a sampling of liquid in the analysis chamber. In the figure, the motion detector comprises a tab 13 located at the inlet hole 6 and mounted on an axis of rotation 14 located above the inlet hole 6 such that a rotation of the axis of rotation resulting from movement of the tab under the effect of liquid entering through the inlet hole 6 generates the delivery of the sampling signal.

Figure 3:
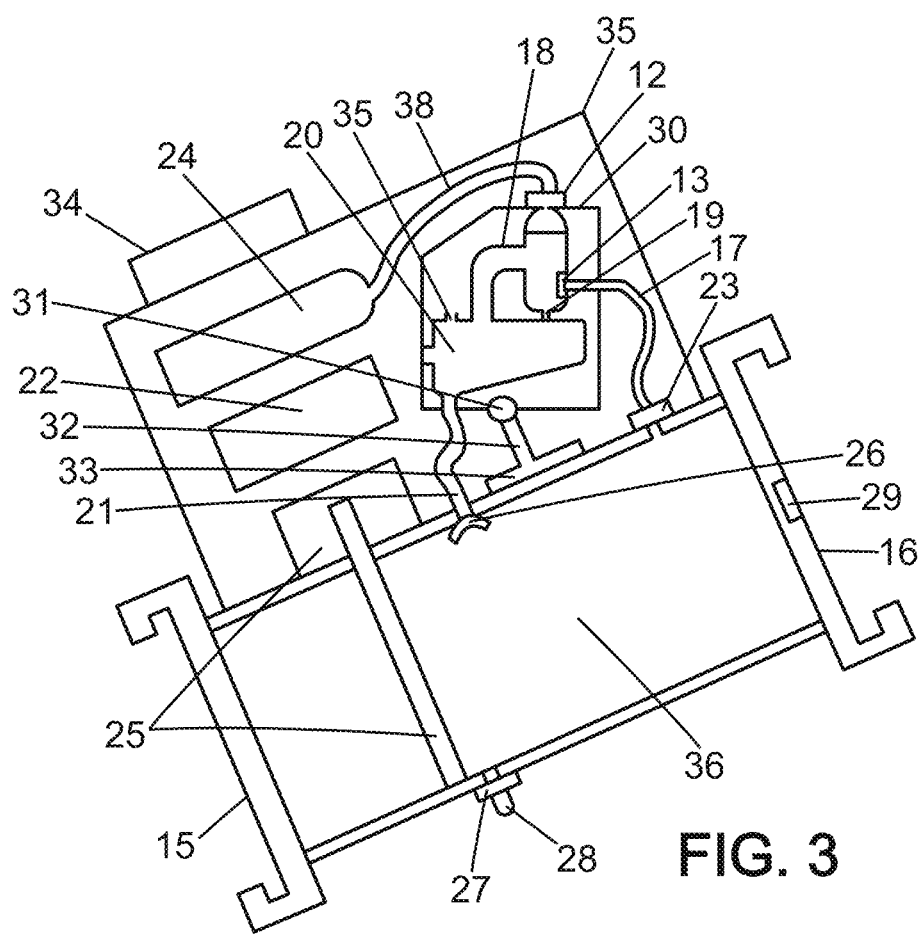
FIG. 3 is a representation of the dispensing device of FIG. 1.

FIG. 3 shows the dispensing device in its entirety, with a dispensing conduit 16 configured to convey liquid between the supply source and the storage tank. The dispensing conduit has a side wall around a central axis, defining a passage for the liquid. The dispensing conduit extends between two opposite ends respectively provided with a first fastener 15 which makes it possible to attach the dispensing device to the storage tank and a second fastener 16 which makes it possible to connect the device to the delivery hose. In particular, the first and second fasteners comprise attachment members configured to engage with complementary attachment members of the supply source and the storage tank respectively. At least the attachment member intended to engage with the complementary attachment member of the supply source is configured to establish a removable attachment.

The second fastener is with a presence sensor 29 capable of delivering a connection signal representative of a connection of the supply source to the dispensing device.

The dispensing conduit comprises a closure system including a solenoid valve 25 which has a passing state in which it allows the flow of liquid in the passage of the dispensing conduit, and a blocking state in which it prevents the flow of liquid in the passage of the dispensing conduit.

The dispensing conduit also comprises a drainage system 28 including a solenoid valve 27 which has an open state in which it allows the flow of liquid through a drainage port comprising a drainage port provided in the side wall of the dispensing conduit, and a closed state in which it prevents the flow of liquid through the drainage port.

The analysis chamber and the odor sensor 24 are part of an analysis system further comprising an inlet pipe 17 extending between the dispensing conduit and the analysis chamber and connected to the inlet hole 6, an outlet pipe 18 connected to the outlet hole 7, and a purge pipe 19 connected to the discharge hole 8. The inlet pipe 17 has a smaller cross-sectional area A than the cross-sectional area B of the outlet pipe 18, and the purge pipe 19 has a smaller cross-sectional area C than the cross-sectional areas of the inlet and outlet pipes. The inlet 17, outlet 18, and purge 19 pipes are flexible.

The analysis system also comprises a first closure member, in the form of a solenoid valve 23, interposed between the inlet pipe and the dispensing conduit. The first closure member has a passing state in which it allows the flow of liquid into the analysis chamber from the inlet pipe, and a blocking state in which it prevents the flow of liquid into the analysis chamber from the inlet pipe. As indicated above, the analysis system also includes the solenoid valve 12 on the upper opening of the analysis chamber and to which is connected a pipe 38 of the odor sensor opening into the odor sensor 24. This solenoid valve 12 forms a second closure member having a passing state in which it allows the flow of fluid, in particular a gas or a gas-liquid mixture, between the upper opening and the odor sensor, and a blocking state in which it prevents the flow of fluid between the upper opening and the odor sensor.

The analysis chamber is thus configured to collect a sample of liquid present in the dispensing conduit.

The analysis system comprises a device for purging the analysis chamber, connected to the outlet 18 and purge 19 pipes and open to the dispensing conduit 36 via a floating ball check valve 26 presenting a passing direction when a pressure in the device for purging is greater than a pressure in the dispensing conduit, and a blocking direction when the pressure in the dispensing conduit is greater than the pressure in the device for purging. In particular, the device for purging comprises a vessel 20 connected to the outlet 18 and purge 19 pipes and to a discharge pipe 21 open to the dispensing conduit 36. The vessel also comprises an air exhaust hole 39.

The analysis system also comprises an orientation system on which the analysis chamber and vessel are mounted so as to orient the analysis chamber in a vertical direction. For example, the orientation system comprises a plate 33 secured to the dispensing conduit 36 from which extends a bracket 32 provided with a ball joint 31. A cage 30 enclosing the analysis chamber and the vessel is mounted on the ball joint.

The dispensing device also comprises a central electronic system 22 which manages the entire dispensing device.

In particular, the central electronic system 22 is connected to the closure system of the dispensing conduit 36 and to the odor sensor 24 of the analysis system, for:
 placing the closure system in the passing state if the odor signal delivered by the odor sensor matches the odor of the liquid intended to fill the storage tank,
 placing the closure system in the blocking state if the odor signal delivered by the odor sensor does not match the odor of the liquid intended to fill the storage tank.

The central electronic system 22 is also connected to the drainage system 28 in order to place the drainage system in the open state if the odor signal delivered by the odor sensor does not match the odor of the liquid intended to fill the storage tank.

The central electronic system 22 may have an active state in which it processes the odor signal delivered by the odor sensor, and a standby state. The dispensing device may then comprise a detection system capable of detecting a situation of supplying liquid, the central electronic system being capable of entering the active state when a supplying situation is detected. In particular, the detection system comprises the presence sensor connected to the central electronic system and the motion detector arranged in the analysis chamber. The central electronic system is then capable of entering the active state when the presence sensor delivers the connection signal and when the motion detector delivers the sampling signal. It may be arranged that the central electronic system in the active state processes the odor signal delivered by the odor sensor after a delay has elapsed.

The entire dispensing device may be placed in a protective housing 35.

A control unit 34 may be attached to the protective housing. The control unit makes it possible to act, in particular by use of a key or a code, on the central electronic system 22 in order to unlock the dispensing device and reset the central electronic system 22 in the event of an error of liquid.

According to one embodiment, the dispensing device comprises fastener 15 to be installed at the outlet of the storage tank 1. It comprises the dispensing conduit 36 for allowing the passage of the liquid to be delivered, which at its other end has fastener 16 for attaching the delivery hose 3.

The floating ball check valve 26 is positioned in the dispensing conduit, as well as the solenoid valve 25 of the closure system. This solenoid valve 25 is controlled by the "intelligent" central electronic system 22 which is placed in the protective housing 35 above the dispensing conduit 36. This central electronic system 22 also controls the odor sensor 24 or electronic nose, the solenoid valve 23 of the inlet pipe 17 of the analysis chamber 5, and the solenoid valve 12 for access to the odor sensor 24, which are placed in the protective housing. It also controls the solenoid valve 27 of the drainage system 28. The central electronic system 22 receives information from the presence sensor 29 and from the motion detector via the pivoting tab 13 placed in the analysis chamber 5.

Also located in the protective housing is the cage 30 in which the analysis chamber 5 and the vessel 20 are attached.

To enable this cage 30 to be plumb, it is fixed to the ball joint 31 at the end of the bracket 32 fixed on the plate 33 which itself is fixed on the dispensing conduit 36. Here are also located the inlet pipe 17, the outlet pipe 18, the purge pipe 19, and the drainage pipe 21. The control unit (34) is located on this protective housing.

The dispensing device 2 is installed at the inlet of the storage tank 1. It is composed of a tapping-off point to the inlet pipe 17 which allows supplying the analysis chamber 5 with the liquid that is to be delivered. The analysis chamber is a container with the inlet hole 6 and the outlet hole 7 as well as the discharge hole 8 for its complete purging. The inlet hole 6 must be at a lower level than outlet hole 7 in order to have a reserve of liquid for the duration of the analysis of the liquid by the odor sensor. The analysis chamber also has the upper opening 11 in its upper portion, for the suctioning by the odor sensor 24. The inlet pipe 17 has a smaller cross-sectional area A than the cross-sectional area B of the outlet pipe 18, in order to prevent the level in the analysis chamber from reaching the upper portion of the analysis chamber. The purge pipe 19 and the outlet pipe 18 are connected to the vessel 20 to allow the storage and flow of the liquid through the discharge pipe 21 after the analysis is completed. The analysis chamber 5 is also provided with the detection system which makes it possible to detect the arrival of liquid in order to activate the central electronic system 22. According to this embodiment, the detection system comprises the tab 13 which is placed just after the inlet hole 6. The liquid which arrives with a certain flow rate pushes directly against this tab which, under the pressure, pivots on its axis of rotation 14 and triggers an electrical sampling signal. This sampling signal informs the central electronic system 22 that it must open the solenoid valve 12 between the analysis chamber 5 and the odor sensor 24. A delay allows the analysis chamber to clean itself with the new liquid and allows the odor sensor to suction in the old odors. Then, after a few seconds, the odor sensor draws air into the analysis chamber 5 in order to recognize or not recognize the characteristics of the expected liquid.

Two alternatives are possible.

In the first case, the analysis of the odor sensor 24 confirms that the analysis conforms to what is expected in the storage tank 1; it sends this information to the central electronic system 22 which orders the closing of solenoid valve 12 to protect the odor sensor, orders the closing of solenoid valve 23 of the analysis chamber inlet, and orders the opening of solenoid valve 25 of the closure system in order to allow the liquid to pass through the dispensing device so that delivery can take place. The liquid flows, then, as soon as the end of delivery is reached, the level of liquid in the dispensing device decreases which allows the floating ball check valve 26 to descend and allows the dispensing conduit and the vessel 20 to drain via the discharge pipe 21. As the delivery to the storage tank 1 has completed, the individual withdraws the delivery hose 3 from the dispensing device; the detection sensor 29 notes this disconnection, sends this information to the central electronic system 22 which orders solenoid valve 25 of the closure system to close off the passage of the dispensing conduit, and orders the opening of solenoid valve 23 of the chamber inlet for a new analysis; the programmed system undertakes a phase of "cleaning" the stagnant vapors in the chamber by a suctioning for a few moments carried out by the pumping of the odor sensor before it goes on standby.

In the second case, the analysis of the odor sensor indicates that the liquid does not conform to what is expected in the storage tank 1; the odor sensor sends this information to the intelligent electronic system 22 which orders the closing of solenoid valve 12 of the second closure member to protect the odor sensor, orders the closing of solenoid valve 23 of the first closure member of the inlet of the analysis chamber 5, triggers a sound alert and/or light alert or other alert and locks down the system to prevent any further intervention without it being unlocked by using a key or a code for example. Another individual must come with the key or the code, must first place a container at the drain port of the draining system 28 in order to be able to collect the liquid from the delivery hose 3. Then this individual must of course close the bladder of the truck 4 containing the non-compliant liquid and must then unlock the system using the code or the key on the unit 34. The central electronic system 22 orders the opening of solenoid valve 27 of the drainage system, the liquid flows into the container, then as soon as the sleeve begins to drain, this allows the floating ball check valve 26 to descend and allows emptying the dispensing conduit and vessel 20. Once the purging of the delivery hose 3 has completed, the individual withdraws it from the second fastener 16; the detection sensor 29 notes this disconnection and sends this information to the central electronic system 22 which orders the closing of solenoid valve 27 of the drainage system, and orders the opening of solenoid valve 23 of the first closure member of the chamber inlet for a new analysis; the programmed system undertakes a phase of "cleaning" the stagnant vapors in the chamber by a suctioning for a few moments carried out by the pumping of the odor sensor before is goes on standby.

For this purpose, the dispensing device may be permanently installed on the storage tanks intended to receive the delivered liquid. The dispensing device may be placed behind the area where handling occurs during delivery. The professional who makes the delivery does not make any changes to his work habits and therefore cannot damage the system. The system will therefore simply make it possible to check automatically whether the person has made an error and to authorize or prevent the delivery of liquid.

The dispensing device can therefore be placed on the inlet of the storage tank. The first fastener preferably provides a fixed attachment to the storage tank. The odor sensor is thus fixed and protected and therefore cannot be damaged. The dispensing device is completely autonomous and does not require any human handling in order to test the liquid, preventing any risk of error. The dispensing device is installed downstream of the supply source placed at a high point upstream, the gravitational force and naturally-induced pressure allowing the filling of the analysis chamber.

Alternatively, the attachment could be removable.

The elements are controlled completely autonomously by the central electronic system 22 so as to leave no room for human error.

The operation consists of connecting the delivery hose which is used to transfer the liquid and opening the bladder of the truck for example, so that the delivery hose fills with the liquid to be delivered. This allows bringing the product to be analyzed to the dispensing device. The connection of the delivery hose to the dispensing device is sensed by the presence sensor 29 which, without limitation, may be a contact detection system or contactless detection system of the RFID type for example, which transmits the presence information to the central electronic system. The central electronic system enters an active state and establishes an initial state.

The liquid flowing in the delivery hose is blocked by the main controlled closure system which, in the embodiment shown and without limitation, is a solenoid valve. A small bypass is located before this main solenoid valve and is connected to the inlet pipe of cross-sectional area A which allows some of the liquid to be sampled from the delivery hose. This inlet pipe directs the liquid toward the inlet hole of the analysis chamber which will therefore contain some of the liquid contained in the delivery hose.

The analysis chamber is provided with a motion detector to detect the arrival of liquid, which may be a tab positioned just after the inlet hole of the analysis chamber and which will pivot around an axis of rotation under the action of the liquid entering the chamber. This axis of rotation transmits the sampling signal during its movement, to the central electronic system which orders the opening of the controlled closure system which, in the embodiment shown and without limitation, is a solenoid valve and which is placed on the pipe that connects the odor sensor to the upper opening of the top portion of the analysis chamber. When this solenoid valve opens, this first allows the suction of vapors contained in the analysis chamber in order to discharge residual odors from a previous delivery. Then, after a delay, the central electronic system orders the odor sensor to suction in the vapors of the new liquid present in the analysis chamber, in order to carry out the analysis.

The outlet pipe of cross-sectional area B, larger than the inlet pipe of cross-sectional area A, creates an outlet from the analysis chamber and is positioned higher than the inlet hole so that there is a certain controlled amount of liquid because the level of liquid can never exceed the level of the outlet, this being so in order to protect the odor sensor.

Another protection of the odor sensor against possible splashes but allowing vapors to pass through is provided in the analysis chamber by the protection plate, in the form of a perforated grid, just above the level of the outlet pipe of cross-sectional area B.

The excess liquid which passes through this outlet pipe of cross-sectional area B is stored in the vessel provided for this purpose.

The purge pipe of cross-sectional area C located in the bottom, which is for example conical, at the base of the analysis chamber, having a smaller cross-sectional area than areas A and B, allows the analysis chamber to be purged by discharging the liquid into the same vessel once the analysis is complete and the analysis chamber is no longer being supplied with liquid through the inlet pipe.

The floating ball check valve located below the vessel is joined by its shape, its material, and the pressure of the liquid contained in the dispensing conduit, to the port together with the vessel to prevent any liquid from rising back up into said vessel.

The odor sensor therefore analyzes the liquid contained in the chamber.

If the liquid in the chamber matches the liquid expected by the tank, the odor sensor transmits this information to the central electronic system which orders the main closure system to open for delivery.

If the liquid in the chamber does not match the liquid expected by the tank, the odor sensor transmits this information to the electronic system which locks down the dispensing device by ordering the closing of the solenoid valve of the second closure member to protect the odor sensor and orders the closing of the solenoid valve of the first closure member so that the analysis chamber is no longer supplied with liquid through the inlet pipe. The central electronic system triggers an alarm to signal the error. Delivery is not possible. The dispensing device may be arranged so that it can only be unlocked by the intervention of another individual on the control unit, by using a key or a code.

One of the advantages of this system is that errors can no longer be concealed.

Once the device has been unlocked using the key or code, the sleeve must be emptied.

If the liquid in the storage tank can accept a tiny amount of contamination, the central electronic system then orders the opening of the solenoid valve of the closure system to purge the liquid contained in the delivery hose and in the vessel, directly into the storage tank.

Or, if the liquid in the storage tank cannot accept any contamination, it is first necessary to connect a container to the drainage port of the dispensing conduit, indicate to the control unit that the container is connected, and the central electronic system orders the opening of the solenoid valve of the controlled drainage system, which therefore makes it possible to empty the delivery hose, the analysis chamber, and the contents of the vessel. Secondly, as soon as the delivery hose is disconnected from the dispensing device, the presence sensor sends this information to the central electronic system which orders the opening of the solenoid valve of the first closure device to allow the next liquid to be tested to pass through to the analysis chamber; the central electronic system orders a phase of "cleaning" the stagnant vapors in the analysis chamber by a suctioning for a few moments carried out by the pumping of the odor sensor before it goes on standby.

The dispensing device is ready for a new analysis.

The analysis chamber and the vessel, which must be positioned properly vertically, are mounted in the cage attached to the orientation system comprising the ball joint at the end of the bracket attached to the plate. With the plate fixed on the dispensing conduit, the ball joint allows, depending on the inclination of the outlet of the storage tank, a fine-tuned adjustment of the position of the cage for proper operation, a clamping means making it possible to fix the orientation system in a chosen position. Similarly, to accommodate this movement, the inlet, outlet, and purge pipes of the analysis chamber are flexible and of sufficient lengths to accommodate the various rotational movements.

Figure 4:
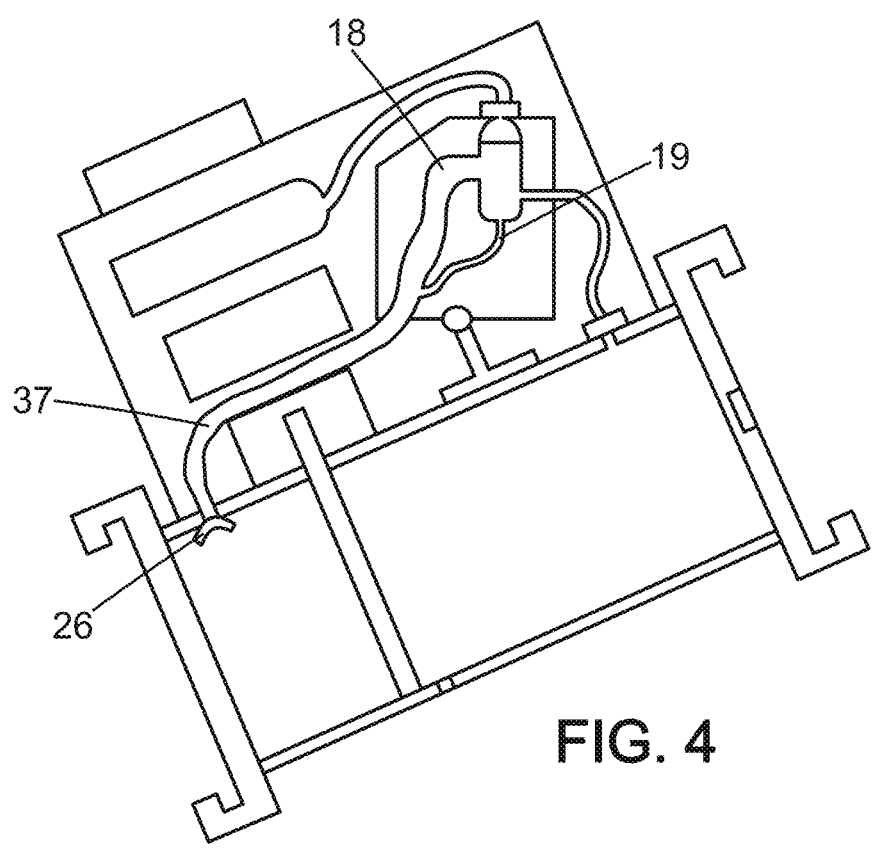
FIG. 4 is a representation of the dispensing device according to a variant.

According to a variant of the invention, shown in FIG. 4, if the liquid accepts minor contamination, the outlet pipe of cross-sectional area B and the purge pipe of cross-sectional area C can be directly connected to the discharge pipe after the solenoid valve of the closure system, so that the excess from the analysis chamber goes directly into the storage tank without being stored in a vessel while awaiting the result of the analysis. In this case, there no longer is a vessel and the floating ball check valve is positioned at this discharge. The solenoid valve of the inlet pipe, controlling the flow of liquid into the analysis chamber, becomes superfluous.

Figure 5:
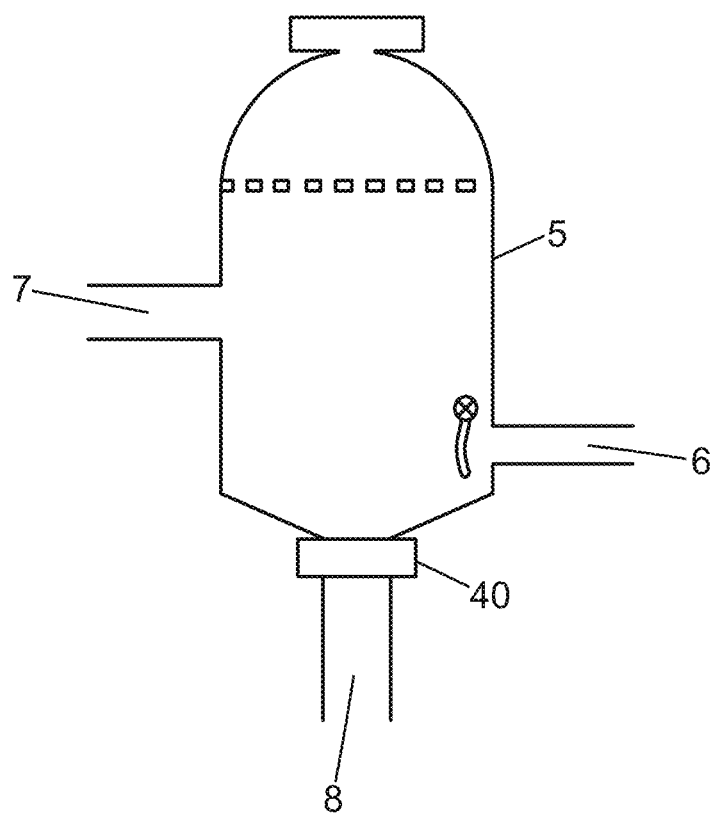
FIG. 5 is a representation of a representative variant of the analysis chamber.

According to another variant of the invention, shown in FIG. 5, to accelerate the rinsing of the analysis chamber, the discharge pipe may be of larger cross-sectional area in order to accelerate the flow rate but is equipped at its base with a closure system controlled to trigger rapid drainage of the chamber at the appropriate time.

According to another variant, the axis of rotation of the motion detector transmits a sampling signal during its movement, to the central electronic system which, after a delay, orders the closing of the controlled closure system which, without limitation, is a solenoid valve located before the inlet pipe of the analysis chamber. A first delay allows the analysis chamber to be completely filled with liquid. After a second delay which allows the analysis chamber to be completely emptied, the electronic system orders the opening of the solenoid valve to allow liquid once again to enter for a new rinsing of the chamber. This operation may be provided by the system a sufficient number of times to eliminate all traces of the previous liquid.

The invention has the following characteristics:

an analysis chamber consisting of an inlet pipe (17) whose opening is actuated by a controlled closure system (23) and supplied with liquid by a bypass line from the delivery hose (3), with an outlet pipe (18), a purge pipe (19), a protective grid (10), a fluid presence detection system which can be a motion detector designed with a pivoting tab (13), an access (11) whose opening is controlled by a controlled closure system (12) so as to connect the analysis chamber to an electronic nose odor sensor (24) for characterization of the liquid to be tested, a vessel which will collect the liquids issuing from the outlet (18) and purge (19) pipes and having a discharge pipe (21) for draining at the appropriate time as well as an air exhaust hole (39) to let air out, a floating ball check valve (26) of which the shape and material can act as a seal when the liquid in the delivery hose pushes it back and allowing the vessel to be drained into the rigid pipe (36) when it is emptying, a main controlled closure system (25) allowing or not allowing the passage of the liquid to be delivered, depending on the characterization of the liquid, a control unit (34) which makes it possible to act on the autonomous electronic system (22) in order to unlock the device and reset the system in the event of an error of liquid, a drainage system (28) controlled by the control unit (34) and actuated by a controlled closure system (27) to drain in the event of an error of liquid, a presence detector (29) placed on the device, for activating the system and placing it on standby, an odor sensor (24), the outlet pipe (18) and the purge pipe (19) will flow into a drainage pipe (37) downstream of the controlled closure system (25), which eliminates the need for the vessel (20).

According to specific arrangements:

said analysis chamber is composed of four holes, three of them connected to the three bypass pipes (17) (18) (19); said pipes are defined by three different cross-sectional areas A, B, and C, area A being smaller in size than area B, and area C smaller in size than areas A and B; said cross-sectional area A corresponds to the cross-sectional area of the bypass inlet pipe (17) of the chamber, which is located in the lower portion of the chamber, through which the liquid to be tested enters said analysis chamber; said cross-sectional area B corresponds to the cross-sectional area of the bypass pipe of the outlet (18) of said analysis chamber, located at a height greater than the hole of cross-sectional area A, allowing the filling of the chamber with a certain volume of liquid and also allowing the discharging of the liquid during the filling of the chamber when it reaches the horizontal diameter of the hole of cross-sectional area B so as not to fill the chamber in its entirety; the height of said hole of cross-sectional area B defines the level of maximum filling of the chamber with liquid in order to prevent the liquid from reaching the odor sensor; said cross-sectional area C corresponds to the cross-sectional area of the bypass pipe of the purge hole (19) located in the conical portion of the bottom of said chamber for completely purging said chamber; the fourth hole is an access (11) in the top portion of the chamber which receives the pipe (38) of the odor sensor in order to suction the vapors of the liquid contained in said analysis chamber, the central electronic system (22) will be activated by the presence detector (29) which will inform it of the connection of a delivery hose (3) to the device and by the motion detector (13) which will inform it of a filling in progress in the chamber, said presence detector also informing the electronic system (29) of the disconnection of the delivery hose (3) in order to return it to standby, the central electronic system (22) activated by the presence detector (29) awaits the signal from the motion detector (13) in the analysis chamber; said motion detector according to one embodiment is a tab, or another means, located at the inlet hole of cross-sectional area A, and is placed on an axis of rotation (14) located above the inlet hole of cross-sectional area A; during the passage of the liquid through the inlet hole (6) this causes movement of the tab and rotation of the axis of rotation (14); said axis of rotation is electrically connected to the intelligent electronic system (22) which triggers the delay before the suctioning by the electronic nose in order to perform the measurement, the security housing (34) enables the system to be unlocked by the use of a key or a code, to order the opening of the controlled closure system (25) in order to empty the device, said analysis chamber is characterized in that a protective plate perforated with multiple holes is located above the maximum fill level for liquid, defined by the level of the hole of cross-sectional area B and sufficiently low below the pipe of the odor sensor to prevent any source of liquid in the odor sensor pipe that could damage the odor sensor, the analysis chamber and the vessel are mounted on an orientation system which may be a ball joint (31) at the end of a small bracket (32) fixed on a plate (33) in order to regain a good vertical position for proper operation; a clamping means allows fixing the orientation system in a chosen position, the inlet (17), outlet (18), and purge (19) pipes of the chamber (5) are flexible and of sufficient lengths to accommodate the various rotational movements necessary for correct alignment of the analysis chamber, the device is installed downstream of the supply container placed at a high point upstream in order to use gravitational force and obtain a naturally-induced pressure in order to supply the analysis chamber with the supply liquid, the device is automatically supplied with liquid by gravitational force, it is this gravitational force that starts it up with a motion detector (13), and a central electronic system (22) uses controlled closure systems (23) (12) (25) (27) so that it can be fully automatic and operate without any human intervention, the main controlled closure system (25) is controlled to allow or not allow delivery by the electronic system (22) depending on the result of the analysis of the liquid in the chamber (5) by the electronic nose (24), said device is totally autonomous and will not require human intervention to carry out analyses via the odor sensor and to generate the actions allowing or not allowing the delivery of liquid; said electronic system will be activated during connection of the delivery hose (3) and the delay until analysis by the electronic nose (24) begins when filling the chamber with liquid; depending on the result of the analysis by the electronic nose, the opening of the controlled closure system (25) is ordered or an alert is generated and the device is locked in the event of an error of liquid, the controlled closure system of the inlet pipe (23) closes as soon as the electronic nose odor sensor (24) has finished its analysis, in order to avoid completely filling the chamber where necessary.

The invention claimed is:

1. A dispensing device for preventing a mixing of liquids, each liquid being characterized by an odor, the dispensing device comprising:
   a dispensing conduit configured to convey a liquid between a supply source and a tank, the dispensing conduit comprising a passage for the liquid and a closure system having a passing state in which said closure system allows the flow of liquid in the passage of the dispensing conduit, and a blocking state in which said closure system prevents the flow of liquid in the passage of the dispensing conduit,
   an analysis system comprising an analysis chamber separate from the dispensing conduit and configured to collect a sample of liquid present in the dispensing conduit, and an odor sensor connected to the analysis chamber and capable of delivering an odor signal representative of the odor of the liquid sample, and
   a central electronic system connected to the closure system of the dispensing conduit and to the odor sensor of the analysis system,
   wherein the central electronic system is capable of:
   placing the closure system in the passing state if the odor signal delivered by the odor sensor matches the odor of the liquid intended to fill the tank, and
   placing the closure system in the blocking state if the odor signal delivered by the odor sensor does not match the odor of the liquid intended to fill the tank.

2. The dispensing device according to claim 1, wherein the dispensing conduit extends between two opposite ends, the ends comprising attachment members configured to engage with respective complementary attachment members of the supply source and of the tank, at least the attachment member intended to engage with the complementary attachment member of the supply source being configured to establish a removable attachment.

3. The dispensing device according to claim 1, wherein the dispensing conduit comprises a side wall around a central axis, defining the passage for the liquid, and a drainage system having an open state in which said drainage system allows the flow of liquid through a drainage port comprising a drainage port provided in the side wall of the dispensing conduit, and a closed state in which said drainage system prevents the flow of liquid through the drainage port, the drainage system being connected to the central electronic system, the central electronic system being capable of placing the drainage system in the open state if the odor signal delivered by the odor sensor does not match the odor of the liquid intended to fill the tank.

4. A supply system comprising a dispensing device according to claim 1 and a supply source, wherein the dispensing device is installed downstream of the supply source placed at a high point upstream so as to use gravitational force and obtain a naturally-induced pressure in order to supply the analysis chamber with liquid.

5. A storage system comprising a dispensing device according to claim 1 and a storage tank, the storage tank having a feed opening on which the dispensing device is mounted.

6. A supply method making use of a dispensing device according to claim 1, the dispensing device being interposed between a supply source and a tank, the method providing for:
   placing the closure system in the passing state if the odor signal delivered by the odor sensor matches the odor of the liquid intended to fill the tank, and
   placing the closure system in the blocking state if the odor signal delivered by the odor sensor does not match the odor of the liquid intended to fill the tank.

7. The supply method according to claim 6, wherein the central electronic system has an active state in which said central electronic system processes the odor signal delivered by the odor sensor, and a standby state, the dispensing device further comprising a detection system capable of detecting a situation of supplying liquid, the central electronic system being capable of entering the active state when a supplying situation is detected, and
   said method providing for placing the active electronic system in an active state when a supplying situation is detected.

8. The supply method according to claim 6, wherein the analysis chamber has a bottom and a side wall extending from the bottom to an upper opening to which the odor sensor is connected, the analysis system comprises:
   an inlet pipe extending between the dispensing conduit and the analysis chamber and open to the side wall of the analysis chamber near the bottom,
   an outlet pipe open to the side wall of the analysis chamber above the inlet pipe and defining a level for the liquid sample,
   a purge pipe open to the bottom of the analysis chamber,
   a first closure member having a passing state in which said first closure member allows the flow of liquid into the analysis chamber from the inlet pipe, and a blocking state in which said first closure member prevents the flow of liquid into the analysis chamber from the inlet pipe, and
   a second closure member having a passing state in which said second closure member allows the flow of fluid between the upper opening and the odor sensor, and a blocking state in which said first closure member prevents the flow of fluid between the upper opening and the odor sensor, and
   said method providing for placing the first closure member in the blocking state as soon as the odor sensor has completed its analysis.

9. The dispensing device according to claim 1, wherein the central electronic system has an active state in which said central electronic system processes the odor signal delivered by the odor sensor, and a standby state, the dispensing device further comprising a detection system capable of detecting a situation of supplying liquid, the central electronic system being capable of entering the active state when a supplying situation is detected.

10. The dispensing device according to claim 9, wherein the detection system comprises a presence sensor connected to the central electronic system and capable of delivering a connection signal representative of a connection of the supply source to the dispensing device, the central electronic system being capable of entering the active state when the presence sensor delivers the connection signal.

11. The dispensing device according to claim 9, wherein the detection system comprises a motion detector arranged in the analysis chamber and connected to the central electronic system, the motion detector being capable of delivering a sampling signal representative of a sampling of liquid in the analysis chamber, the central electronic system being capable of entering the active state when the motion detector delivers the sampling signal.

12. The dispensing device according to claim 11, wherein the central electronic system in the active state processes the odor signal delivered by the odor sensor after a delay has elapsed.

13. The dispensing device according to claim 11, wherein the analysis chamber comprises an inlet hole through which the liquid collected from the dispensing conduit enters the analysis chamber, and wherein the motion detector comprises a tab located at the inlet hole and mounted on an axis of rotation located above the inlet hole such that rotation of the axis of rotation resulting from displacement of the tab under the effect of the liquid entering through the inlet hole causes delivery of the sampling signal.

14. The dispensing device according to claim 1, wherein the analysis chamber has a bottom and a side wall extending from the bottom to an upper opening to which the odor sensor is connected, the analysis system comprises:
- an inlet pipe extending between the dispensing conduit and the analysis chamber and open to the side wall of the analysis chamber near the bottom,
- an outlet pipe open to the side wall of the analysis chamber above the inlet pipe and defining a level for the liquid sample,
- a purge pipe open to the bottom of the analysis chamber,
- a first closure member having a passing state in which said first closure member allows the flow of liquid into the analysis chamber from the inlet pipe, and a blocking state in which said first closure member prevents the flow of liquid into the analysis chamber from the inlet pipe, and
- a second closure member having a passing state in which said second closure member allows the flow of fluid between the upper opening and the odor sensor, and a blocking state in which said first closure member prevents the flow of fluid between the upper opening and the odor sensor.

15. The dispensing device according to claim 14, wherein the inlet pipe has a cross-sectional area A that is smaller than the cross-sectional area B of the outlet pipe, and the purge pipe has a cross-sectional area C that is smaller than the cross-sectional areas of the inlet and outlet pipes.

16. The dispensing device according to claim 14, wherein the analysis chamber comprises a protective plate perforated with multiple holes, located above the outlet pipe.

17. The dispensing device according to claim 14, wherein the analysis system comprises an orientation system on which the analysis chamber is mounted so as to orient the analysis chamber in a vertical direction, the inlet, outlet, and purge pipes being flexible.

18. The dispensing device according to claim 14, further comprising a control unit which makes it possible to act on the autonomous electronic system in order to unlock the device and reset the system in the event of an error of liquid, in particular with the use of a key or a code.

19. The dispensing device according to claim 14, wherein the analysis system comprises a device for purging the analysis chamber connected to the outlet and purge pipes and open to the dispensing conduit.

20. The dispensing device according to claim 19, wherein the device for purging comprises a vessel connected to the outlet and purge pipes and to a discharge pipe open to the dispensing conduit, the vessel having an air exhaust hole.

21. The dispensing device according to claim 19, wherein the device for purging is open to the dispensing conduit via a floating ball check valve presenting a passing direction when the pressure in the device for purging is greater than the pressure in the dispensing conduit, and a blocking direction when the pressure in the dispensing conduit is greater than the pressure in the device for purging.

\* \* \* \* \*